United States Patent [19]

Bible

[11] Patent Number: 5,181,519
[45] Date of Patent: Jan. 26, 1993

[54] DEVICE FOR DETECTING ABNORMAL HEART MUSCLE ELECTRICAL ACTIVITY

[75] Inventor: Christopher T. Bible, Reno, Nev.

[73] Assignee: Caliber Medical Corporation, Reno, Nev.

[21] Appl. No.: 701,780

[22] Filed: May 17, 1991

[51] Int. Cl.$^5$ .............................. A61B 5/0468
[52] U.S. Cl. ....................... 128/704; 128/702
[58] Field of Search ........................... 128/702, 704

[56] References Cited

U.S. PATENT DOCUMENTS

| 3,267,934 | 8/1966 | Thornton | 128/704 |
|---|---|---|---|
| 3,858,034 | 12/1974 | Anderson | 128/704 |
| 3,868,567 | 2/1975 | Ekstrom | 128/704 |
| 4,546,776 | 10/1985 | Bellin et al. | 128/704 |
| 5,003,983 | 4/1991 | Dingwall et al. | 128/704 |
| 5,058,597 | 10/1991 | Onoda et al. | 128/704 |

OTHER PUBLICATIONS

Thaler, Malcomm S., *The Only EKG Book for You'll Ever Need*, J. B. Lippincott & Co., 1988, pp. 8-29.
Pepine, Carl J., "Technical Requirements of Ambulatory ECG Monitoring", *The Journal of Myocardial Ischemia*, Jun. 19, 1989, pp. 8-29.

*Primary Examiner*—Lee S. Cohen
*Assistant Examiner*—J. R. Jastrzab
*Attorney, Agent, or Firm*—Nydegger & Associates

[57] ABSTRACT

A portable apparatus and method for monitoring heart muscle electrical activity includes a plurality of electrical contacts and a monitoring unit. The contacts receive the electrical signals generated by the heart muscle of a patient and transmit the signals to the monitoring unit. A reference axis is established for each signal by the monitoring unit. Predetermined portions of each signal are then used by the monitoring unit to identify the ST segment of the signal which is then compared to the reference axis. Whenever a series of ST segments exhibit an ST deviation from the reference axis which exceeds a predetermined threshold ST deviation, the monitoring unit records data relating thereto which is used for diagnosis of myocardial ischemia.

20 Claims, 3 Drawing Sheets

DEVICE FOR DETECTING ABNORMAL HEART MUSCLE ELECTRICAL ACTIVITY

FIELD OF THE INVENTION

The present invention relates generally to monitoring heart muscle electrical activity. More particularly, the present invention relates to an apparatus and method for detecting abnormal heart muscle electrical activity. The present invention particularly, though not exclusively, relates to an apparatus and method for detecting myocardial ischemia by measuring deviations in the ST segment.

BACKGROUND OF THE INVENTION

A restricted blood supply to the heart muscle is a condition termed myocardial ischemia which is evidenced by abnormal heart muscle electrical activity. Untreated, myocardial ischemia can ultimately result in heart failure. As a result, monitoring of the electrical signals which stimulate the heart muscle is an invaluable diagnostic tool for determining the health of the heart and identifying abnormalities thereof.

When the electrical signal of a heart muscle is plotted over time, it defines a characteristic curve having a waveform which extends periodically above and below a horizontal reference axis conventionally termed the isoelectric line. Each elevation or depression of the signal curve above or below the reference axis respectively is termed a wave and is identified by a letter. There are a total of six waves in each period of the signal which are identified by the letters, P, Q, R, S, T, and U. A straight line connecting two waves of the signal curve is further identified as a segment, while a wave and connecting straight line is termed an interval. Segments and intervals are identified by various combinations of the above-listed letters.

A normal electrical signal of a healthy heart muscle is generally reflected in a regular curve having predictable PR and ST segments and PR, QRS, and QT intervals. Anomalous electrical signals of a heart muscle are reflected by deviations in specific portions of the curve from the predicted norm. Such deviations, and specifically deviations of the ST segment, may be symptomatic of myocardial ischemia.

Conventional electrical monitoring devices of the heart muscle are usually relatively immobile and complex to operate which requires them to be maintained in a central medical facility for operation by skilled personnel. As a result, outpatients at such facilities only receive monitoring periodically and for a short duration. However, diagnosis of myocardial ischemia generally requires the compilation of signal histories for an extended period of time which periodic monitoring does not provide.

Portable monitors for heart muscle electrical activity represent a potential solution to this problem. Unfortunately, satisfactory portable monitors have not been developed which are sufficiently small to enable full mobility of the patient, yet which are sufficiently sophisticated to enable continuous and reliable electrical monitoring of the patient in remote environments. As such, an electrical monitor is needed which specifically monitors electrical signals of the heart muscle and detects abnormal activity thereof. A monitor is needed which enables recording and displaying of relevant diagnostic data relating to anomalous heart muscle electrical signals. Further, such a monitor is needed which is portable, thereby enabling full mobility of the patient while providing continuous effective operation in remote environments.

SUMMARY OF THE INVENTION

The present invention is a device and method for detecting abnormal electrical activity in the heart muscle of a patient. The device comprises a plurality of electrical contacts and a self-contained monitoring unit, which are designed to operate in conjunction with structurally separate data transmission and data display units. The contacts are positionable on the chest of a patient to receive electrical signals which are generated by the electrical activity of the patient's heart muscle. Electrical signals so received are transmitted to the monitoring unit for conversion to meaningful diagnostic data.

Specifically, the present invention recognizes that the ST segment of the heart muscle electrical signal, is a key indicator of myocardial ischemia. The ST segment of a typical healthy heart is a straight line of zero slope on or near a horizontal reference axis. If the ST segment is parallel to the reference axis, but is elevated or depressed by a significant deviation from the reference axis, the heart muscle signal is termed anomalous which may be indicative of an unhealthy heart muscle. Likewise, an ST segment exhibiting a significant positive or negative slope, may further be indicative of an unhealthy heart.

The monitoring unit of the present invention is provided with the requisite electronic circuitry and corresponding software to establish the reference axis for each signal, identify the ST segment of each such signal, and compare the ST segment with the reference axis. Accordingly, the monitoring unit measures the extent to which the ST segment deviates above or below the reference axis. This quantity, which is termed the measured ST deviation, is compared to a predetermined threshold deviation of the ST segment which is stored in the memory of the monitoring unit. When the monitoring unit first detects an ST deviation which exceeds the predetermined threshold ST deviation, the monitoring unit identifies this measured ST segment as an anomalous ST segment deviation initiating an ischemic event. The associated signal is then stored while the monitoring unit continues to search for further measured ST deviations exceeding the threshold ST deviation. Consecutive signals having ST deviations exceeding the threshold constitute an episode. For each episode, the monitoring unit records the first signal of the episode as noted above, the last signal of the episode, and the signal representing the maximum ST deviation of the episode, if there is such a maximum. To supplement these recorded signals, associated data such as slope of the ST segment, duration of the episode and heartbeat rate are also recorded. This data recording procedure is repeated for each occurrence of a new episode.

The recorded signals and associated data can be displayed by transmitting them from the monitoring unit to a remote display unit via a data transmission unit. Upon receiving the recorded signals and associated data from the monitoring unit for each episode, the display unit has the ability to print out the signals in graphical form along with the associated data in a summary report therewith. The display unit can be equipped to receive the output of a plurality of monitoring units from separate patients and from the same or different data transmission units. Each monitoring unit has a unique identification code which is transmitted to the display unit and displayed with the episode to identify the patient associated therewith.

The present device and method have a number of features which facilitate utility by a physician as a tool for the detection and diagnosis of existing or future heart problems. For example, the predetermined threshold ST deviation is adjustable by the physician and is advantageously set such that measured ST deviations greater than the predetermined threshold ST deviation reliably suggest a potential heart problem. The monitoring unit further provides pointers to be displayed with the print-outs of the signals from the display unit which ensure the integrity of the data. A first pointer is provided to identify the point on the PR segment of each period which is used to establish the reference axis. A second pointer is provided to identify that point on each period of the ST segment where the actual ST deviation is measured. If a pointer is absent from a given period of a signal, it indicates that the monitoring unit was unable to determine the corresponding information for that period.

In further accordance with the utility of the present invention, the monitoring unit is designed to be portable. As a result, the mobility of the patient is not restricted by continuous use of the device throughout the patient's range of everyday activities. To facilitate portability, the monitoring unit is sized to affix to the patient and can be powered by a portable battery which has a long life of 96 hours or more due to power conservative operation of the monitoring unit. The data transmission unit can be maintained separate from the monitoring unit and coupled therewith only when downloading and display of recorded data is desired. Thus, portability of the monitoring unit is enhanced by its selective data transmission capability. Because the monitoring unit can operate independent of the transmission and display functions, the patient is not encumbered by the attendant equipment necessary to transmit and perform continuous data displays.

Finally, there is no practical limit to the data recording capabilities of the monitoring unit because, as noted above, it can be periodically downloaded to the data transmission unit whenever memory capacity is reached. Upon downloading, the memory of the monitoring unit is cleared and the unit is immediately available to resume monitoring the electrical signals of the patient's heart. This ensures that a continuous study of the patient's heart for a period of days or even weeks can be performed without significant data storage restraints.

The novel features of this invention, as well as the invention itself, both as to its structure and its operation, will be best understood from the accompanying drawings, taken in conjunction with the accompanying description, in which similar reference characters refer to similar parts, and in which:

DETAILED DESCRIPTION OF PREFERRED EMBODIMENTS

Figure 1:
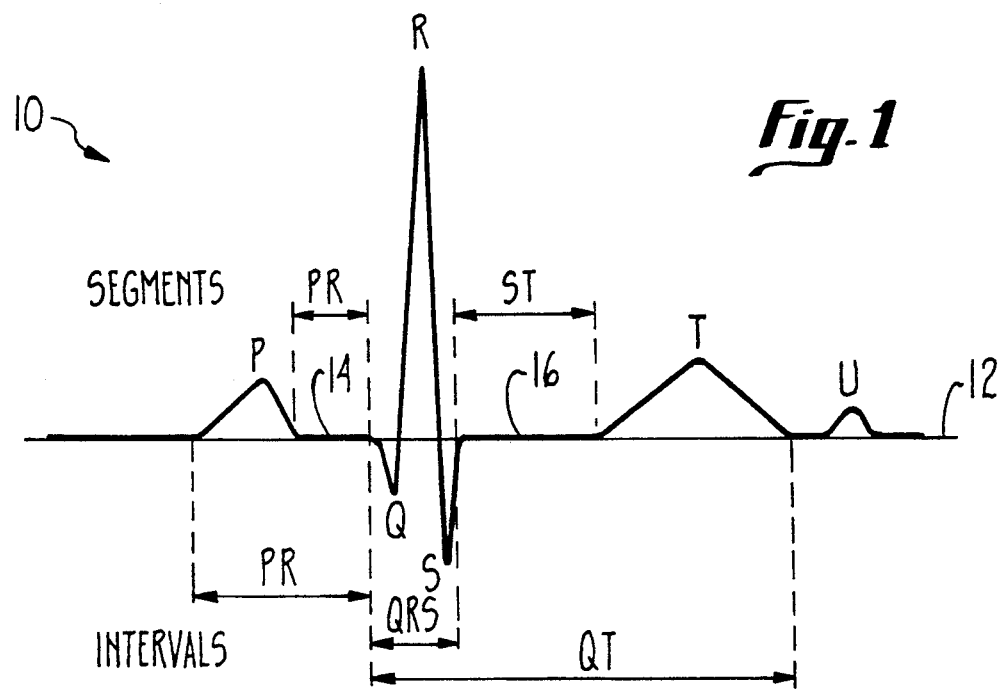
FIG. 1 is a plot of a normal heart muscle electrical signal.

FIG. 1 graphically illustrates a single period of a typical normal heart muscle electrical signal 10 on a one millimeter square grid which is shown blown up here for clarity. The vertical scale of FIG. 1 is the electrical force of the signal, wherein 1 millimeter=0.1 millivolt. The horizontal scale is time, wherein 1 millimeter=0.4 second. The reference axis 12 of the signal, which is conventionally termed the isoelectric line, is established by drawing a horizontal line of zero slope through the PR segment 14. ST segment 16 is noted extending from the end of the S wave to the beginning of the T wave and for a typical healthy heart is characterizable as having zero slope and lying substantially on reference line 12.

Figure 2:
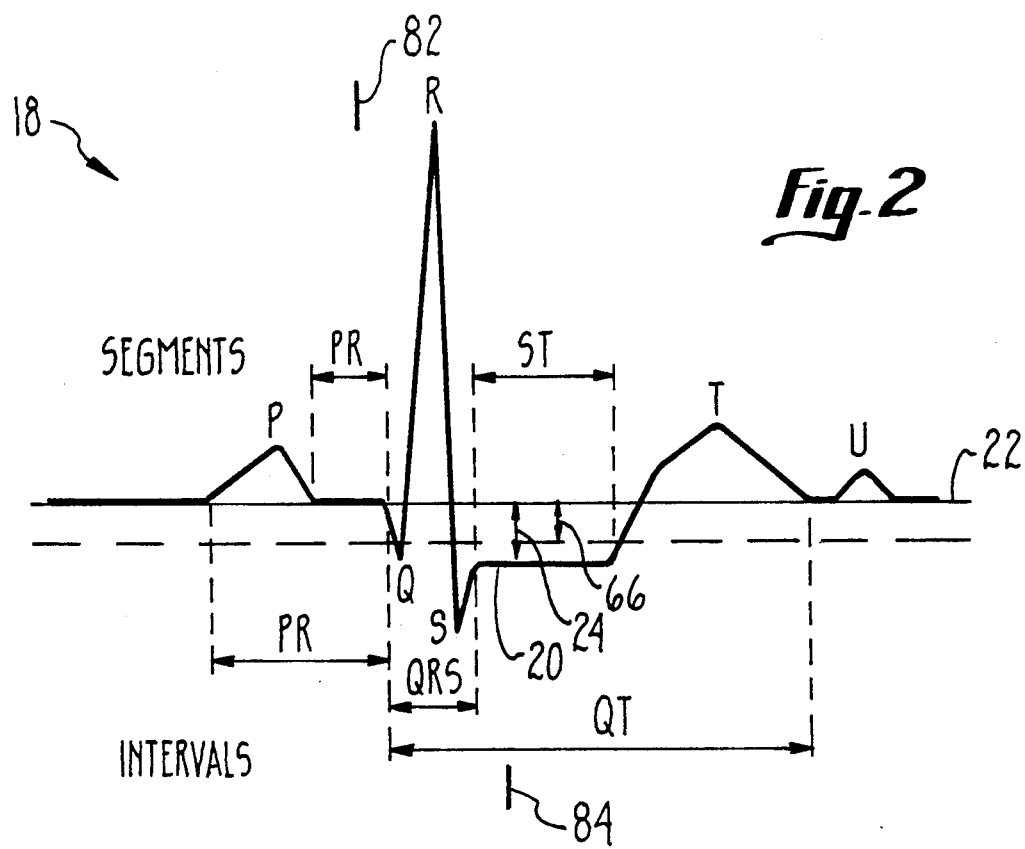
FIG. 2 is a plot of an anomalous heart muscle electrical signal.

FIG. 2 graphically illustrates a single period of an anomalous heart muscle electrical signal 18. The anomalous curve 18 has substantially the same shape as the normal curve 10 of FIG. 1, but the anomalous ST segment 20 is significantly depressed below the reference axis 22 of signal 18. The distance 24 that ST segment 20 deviates from the reference axis 22, either above or below, is termed the ST deviation. In the present case ST deviation 24 is a depression of about 1.5 mm.

Figure 3:
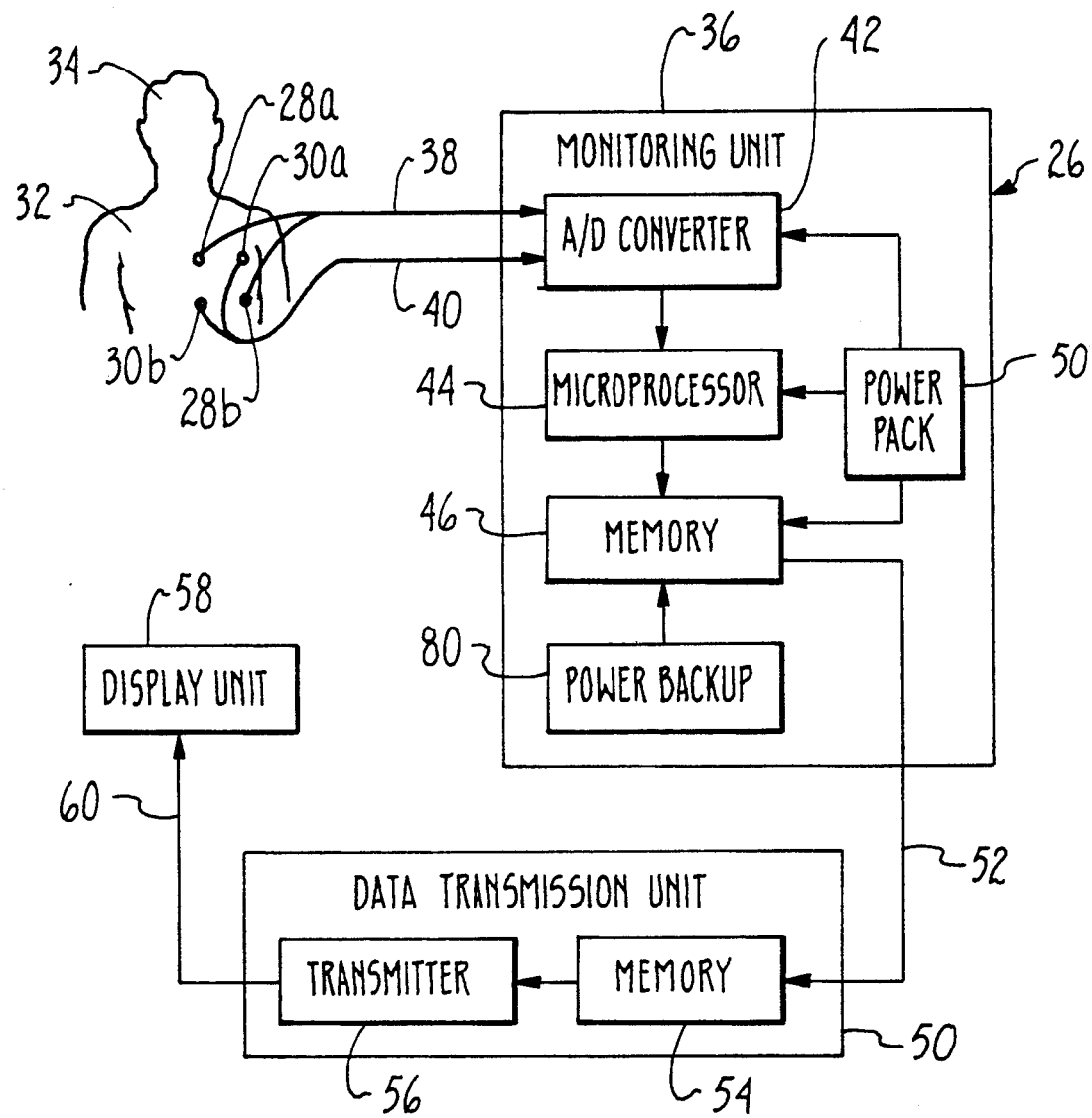
FIG. 3 is a schematic block diagram of the device of the present invention.

FIG. 3 schematically shows the device of the present invention designated generally as 26. Two pairs of conventional electrical contacts 28, 30 are provided which attach to the skin on the chest 32 of patient 34. Although two pairs of contacts 28, 30 are shown here, it is understood that device 26 is operable with a single pair of contacts or any number of contacts greater than shown. The positioning of the contacts 28a, 28b, 30a, 30b is within the purview of the skilled artisan such that they are best able to receive the electrical signals of the heart muscle.

Each pair of contacts 28, 30 is an electrical pick-up in communication with monitoring unit 36 via lines 38 and 40 respectively. Although contact pairs 28, 30 are intended to detect the same heart muscle activity, each pair may measure a substantially different signal because of their different positions relative to the heart of patient 34. Accordingly, lines 38 and 40 define separate data channels being fed to monitoring unit 36. In the preferred embodiment, monitoring unit 36 is capable of processing a plurality of data channels separately. However, device 26 will be described hereafter in the context of a single data channel 38, it being understood that the description of data channel 38 applies similarly to data channel 40 or any additional data channels which result when additional contacts are employed.

Monitoring unit 36 is provided with internal components which enable it to electronically process heart muscle electrical signals transmitted from contacts 28, 30 and convert them into meaningful diagnostic data according to a method described hereafter. Internal components of monitoring unit 36 include an analog to digital converter 42, a microprocessor 44, and a memory 46. A power pack 48, which may be a conventional 9 volt battery, powers monitoring unit 36.

Electrical communication is selectively provided between memory 46 of monitoring unit 36 and a data transmission unit 50 across a releasable linkage 52 such as an infrared optical coupling so that monitoring unit 36 and data transmission unit 50 can be maintained structurally separate. Data transmission unit 50 is provided internally with a memory 54 and a transmitter 56 which is preferably a telephone modem.

Data transmission unit 50 is in selective communication with display unit 58 via line 60 which is preferably a telephone line linkable to transmitter 56. Display unit 58 is preferably a central processing unit (CPU) in command of conventional printers capable of generating strip recordings in the form of FIGS. 1 and 2 as well as associated data for compilation in a report. Display unit 58 may be further provided with a capability to transmit the reports via facsimile equipment to physicians' remote offices.

Figure 4:
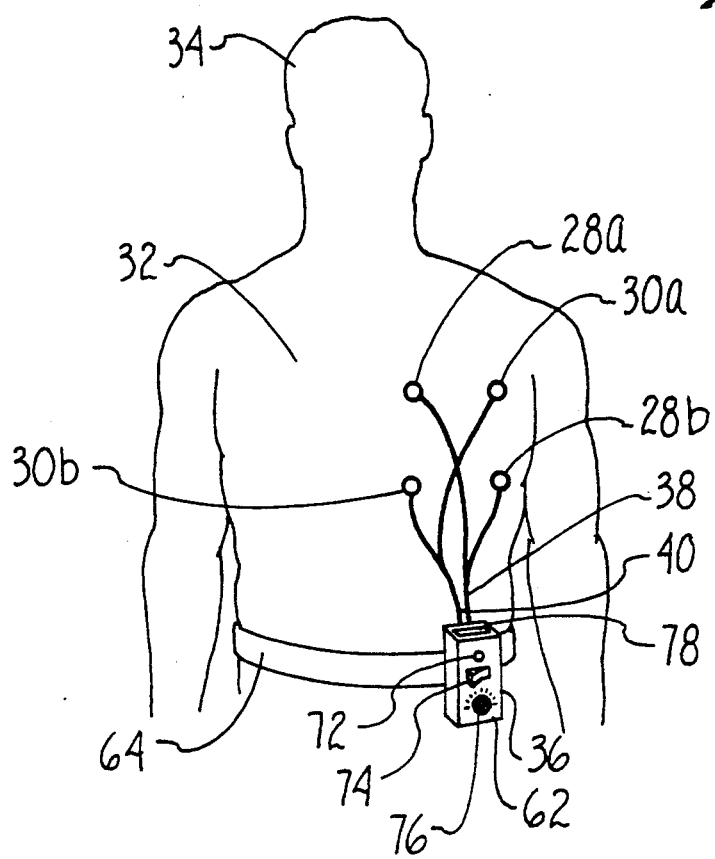
FIG. 4 is a perspective of the monitoring unit in place on the body of a patient.
Figure 5:
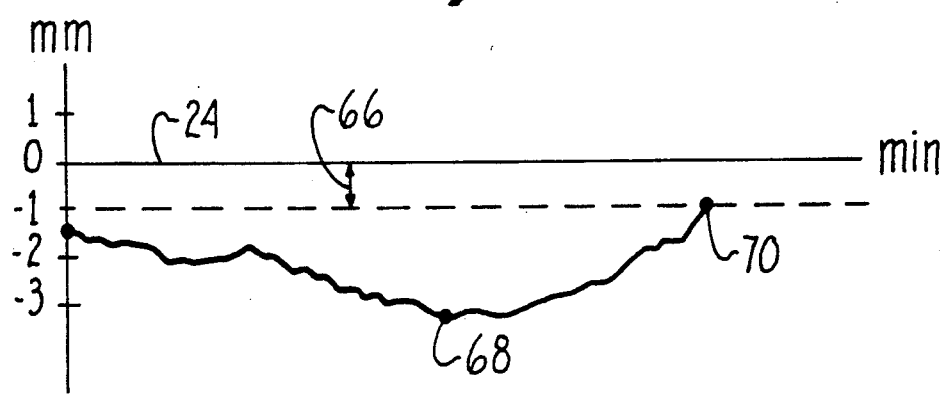
FIG. 5 is a plot of the ST trend diagram.

FIG. 4 shows a preferred embodiment of the present invention as it is worn on the body of patient 34. Monitoring unit 36 is housed within a self-contained enclosure 62 which is sufficiently small and lightweight to be portable. As shown herein, enclosure 62 is attachable to the patient 34 by a belt 64. Alternatively, the enclosure 62 can be clipped to or inserted in the patient's clothing during everyday use of the monitoring unit 36. The monitoring unit 36 is intended to be continuously used in this fashion without substantially restricting the mobility or range of activities of the patient.

The method of operation of the present invention is now described in gross with reference to FIGS. 1-5. In operation, monitoring unit 36 is first positioned on the patient 34 by attaching contacts 28a, 28b to the chest 32 and attaching enclosure 62 to the patient 34 as shown in FIG. 4. Referring back to FIG. 3, line 38 is then secured between contacts 28a, 28b and monitoring unit 36. Power is supplied to monitoring unit 36 from power pack 50, placing unit 36 in an operational state.

When the myocardial cells of the heart muscle produce an electrical signal of the form as shown for example in FIG. 1, the signal 10 is received by contacts 28a, 28b and transmitted via line 38 in an analog form to monitoring unit 36. Analog to digital converter 42 digitizes the signal 10 and sends it to microprocessor which establishes the reference axis 12 by locating the PR segment of signal 10. Microprocessor 44 then locates the ST segment 16 of signal 10 and measures the ST deviation of the signal relative to the reference axis 12. Since the ST deviation in FIG. 1 is substantially zero, it does not exceed the threshold deviation. Therefore, signal 10 is not stored and monitoring unit 36 continues to receive the next signal for processing in this same manner.

If the next signal is of the form shown in FIG. 2, a significant ST deviation 24 is detected by monitoring unit 36. Microprocessor 36 compares measured ST deviation 24 to a fixed threshold ST deviation 66 which is predetermined and stored in memory 46. Threshold ST deviation 66 is indicated by the horizontal dashed line in FIG. 2. The threshold ST deviation is advantageously predetermined such that measured ST deviations greater than the predetermined threshold ST deviation reliably suggest myocardial ischemia. Thus, measurements of ST deviations exceeding the threshold serve as a notice to obtain close medical attention. For measuring depressions, a threshold ST deviation is generally preselected greater than about 0.5 mm, preferably greater than about 1 mm, and most preferably between about 1 and 1.5 mm below the reference axis 22. In contrast, for measuring elevations, a threshold ST deviation is generally preselected somewhat higher than that for a depression. A typical threshold is on the order of about 2.0 mm.

Once monitoring unit 36 determines that signal 18 has initiated an event of interest, monitoring unit 36 stores signal 18 in memory 46 while microprocessor 44 receives consecutive subsequent signals.

If microprocessor 44 continues to measure deviations of subsequent consecutive signals which exceed the threshold deviation for an arbitrary preselected minimum time period (typically about 1 minute), the entire sequence of signals is designated an ischemic episode and the following data relating to the episode are retained in memory 46: value of the reference axis, value of the threshold ST deviation, ST deviation of each signal, a separate strip (6 seconds in duration) for the signal initiating the episode, terminating the episode, and having the maximum ST deviation of the episode (if any), slope of the ST segments of the initiating, terminating and maximum signals, duration of the episode, and heart rate throughout the episode.

The data is retained in memory 46 until capacity is reached, at which time, monitoring unit 36 is removed from patient 34 and placed in communication with data transmission unit 50. Memory 46 transmits data across linkage 52 to data transmission unit 50 which in turn stores the data in memory 54 for transmission by transmitter 56 to display unit 58. Once memory 46 is downloaded, it is cleared, and capable of resuming data storage. Thus, monitoring unit 36 is returned to patient 34 at this time for continued operation.

Display unit 58 can produce all of the above recited numeric data in report form along with full print-outs of the six-second strips upon receipt from data transmission unit 50. Additionally an ST trend plot shown in FIG. 5 can be produced from a compilation of the ST deviation data for each signal. In the plot, the measured ST deviation is the vertical axis and time is the horizontal axis. The initiating ST deviation is denoted 24, the maximum ST deviation is 68, and the terminating deviation is 70. It is apparent that the episode initiates and terminates at the threshold deviation 66.

The above-described data recording procedure is repeated for each successive episode. The amount of data recorded in an episode or a series of episodes is not limited to the available memory 46 in monitoring unit 36 because of the downloading capability to transmission unit 50. Therefore, continuous studies of the heart can be performed which exceed the limitations of the memory 46 in monitoring unit 36.

In practice a number of additional operational features are built into the monitoring unit 36 which expand its data processing capabilities and insure the integrity of the data obtained thereby. Although microprocessor 44 has been described for simplicity as utilizing individual heart muscle electrical signals to establish when an ST threshold deviation is exceeded, in practice, an episode is not initiated until the average deviation of multiple consecutive signals exceeds the threshold deviation. By using the average, isolated aberrant or erroneous signal measurements are discounted. Thus, for example, if measured ST deviation 24 was only a single isolated deviation, microprocessor 44 would recognize that no episode had occurred and eliminate the strip containing signal 20 from memory 46.

Monitoring unit 36 also averages the QRS interval width of multiple signals in microprocessor 44 and uses this average to discard invalid signals. When microprocessor 44 identifies a signal with an excessive QRS interval width relative to the average, microprocessor 44 collects no further ST segment data on that signal.

Other signal rejection criteria used by microprocessor 44 include excessively narrow signal, premature signal, reference axis wander, absence of R wave, or signal pause. Signals evidencing any or all of these characteristics are rejected and data recording does not resume until the signals stabilize. Similarly, if an ST segment is identified as having an excessive slope, that segment will be rejected from the collected data.

The monitoring unit 36 has been described above for operation in an automatic mode. However, patient 34 can activate the ST segment data acquisition and recording function of monitoring unit 36 at any time he or she is symptomatic. Referring to FIG. 4, patient 34 can record a strip without monitoring unit initiation simply by depressing an activation button 72 on enclosure 62 in communication with microprocessor 44. When the strip is displayed by unit 58, it is identified as resulting from patient activation.

Enclosure 62 is further shown in FIG. 4 having two external switches 74, 76 on its face which are in communication with microprocessor 44. Switches 74, 76 may be set by patient 34 or a physician to manually specify operating parameters of the monitoring unit 36. Specifically, dip switch 74 is provided to manually select between a plurality of time points after the S wave terminates at which to measure the ST segment deviation. In the preferred embodiment, ST deviation can be measured at either 60 or 80 milliseconds after termination of the S wave.

Switch 76 provides for one of two modes for establishing the threshold ST deviation. In the first mode, i.e., the absolute mode, the threshold deviation is set at a fixed value which is projected to be indicative of ischemia. In a preferred embodiment, switch 76 has the setting options of 1.0 and 2.0 mm for ST depression and 1,2,3 or 4 mm for ST elevation. The settings are selected on the basis of the patient's individual signal characteristics. In the second mode, i.e. the delta mode, the value of the threshold deviation for ST segment depression is allowed to float as a function of a patient's computed normal depression. Thus, if a patient consistently indicates an ST depression of 0.5 mm and switch 76 setting is on 1.0 mm in the delta mode, the threshold depression which will initiate an episode is 1.5 mm.

To enhance data integrity, warnings are provided to patient 34 when maintenance of device 26 is required. Monitoring unit 36 has an audible alarm (not shown) and a visual display 78 such as an LCD in enclosure 62 shown in FIG. 4 which indicate when power pack 50 shown in FIG. 3 is low, input signals from contact pairs 28, 30 are lost, or memory 46 is full. Likewise, data transmission unit 50 is provided with an alarm to indicate if data transfer from monitoring unit 36 or to display unit 58 is malfunctioning.

When power pack 50 is low, microprocessor 44 blocks operation of the monitoring unit 36 to prevent loss of data until power pack 50 is replaced. Furthermore, memory 46 cannot be accessed until this condition is corrected. An additional long life power backup 80 is provided to memory 46 in the event of complete power failure or during changing of power pack 50 to ensure that no data is lost. A preferred backup is a lithium battery having a battery life of many years.

Pointers 82, 84 shown on FIG. 2 are provided by microprocessor 44 with strip data to enable validation of the reference axis 22 and ST segment deviation 24 measuring points respectively. Pointers 82, 84 are printed directly on the strip when produced by display unit 58.

While a particular Device for Detecting Abnormal Heart Muscle Electrical Activity as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. An apparatus for monitoring heart muscle electrical activity of a patient comprising:
   means positionable on the body of a patient for receiving electrical heart muscle signals generated by the patient;
   means for establishing a reference axis relative to each of said signals;
   means for identifying an ST segment in each of said signals;
   means for measuring an ST deviation from said reference axis of each said ST segment and comparing said ST deviation to a predetermined threshold ST deviation; and
   means for selectively storing an anomalous ST deviation when said anomalous ST deviation exceeds said predetermined threshold ST deviation and excluding ST deviations below said predetermined threshold ST deviation.

2. An apparatus for monitoring heart muscle electrical activity of a patient comprising:
   means positionable on the body of a patient for receiving electrical heart muscle signals generated by the patient;
   means for establishing a reference axis relative to each of said signals;
   means for identifying an ST segment in each of said signals;
   means for measuring an ST deviation from said reference axis of each said ST segment and comparing said ST deviation to a predetermined threshold ST deviation wherein said measuring means is further for determining an average ST deviation from a plurality of said ST deviations in sequence and for comparing said average ST deviation to said predetermined threshold ST deviation; and
   means for storing an anomalous ST deviation exceeding said predetermined threshold ST deviation wherein said storing means is further for storing a plurality of anomalous ST deviations in sequence having an average ST deviation exceeding said predetermined threshold deviation to the exclusion of ST deviations having an average ST deviation below said predetermined threshold ST deviation.

3. An apparatus for monitoring heart muscle electrical activity of a patient as recited in claim 2 wherein said storing means is further for storing a first signal and a last signal of a sequence of heart muscle electrical signals embodying said plurality of anomalous ST deviations in sequence to the exclusion of signals embodying ST deviations having an average ST deviation below said predetermined threshold ST deviation.

4. An apparatus for monitoring heart muscle electrical activity of a patient as recited in claim 3 wherein said storing means is further for storing a signal corresponding to a maximum ST deviation of said sequence of heart muscle electrical signals embodying said plurality of anomalous ST deviations in sequence.

5. An apparatus for monitoring heart muscle electrical activity of a patient as recited in claim 3 further comprising means for displaying said first signal and said last signal of said sequence of heart muscle electrical signals embodying said plurality of anomalous ST deviations in sequence and means for transmitting said first signal and said last signal from said storing means to said display means.

6. An apparatus for monitoring heart muscle electrical activity of a patient as recited in claim 2 wherein said measuring means is further for measuring a heart rate time history of said patient while measuring said plurality of anomalous ST deviations in sequence and wherein said storing means is further for storing said heart rate time history.

7. An apparatus for monitoring heart muscle electrical activity of a patient as recited in claim 2 further comprising means for displaying said stored ST deviation exceeding said predetermined threshold ST deviation and means for transmitting said stored ST deviation from said storing means to said display means.

8. An apparatus for monitoring heart muscle electrical activity of a patient as recited in claim 2 further comprising means for displaying said stored plurality of anomalous ST deviations in sequence on a plot versus time and means for transmitting said plurality of anomalous ST deviations in sequence from said storing means to said display means.

9. An apparatus for monitoring heart muscle electrical activity of a patient as recited in claim 2 wherein said measuring means is further for measuring a slope of said ST segment relative to said reference axis.

10. An apparatus for monitoring heart muscle electrical activity of a patient comprising:
    a plurality of electrical contacts positionable on the body of a patient to receive electrical heart muscle signals generated by the patient; and
    a monitoring unit having a microprocessor in electrical communication with said plurality of electrical contacts to establish a reference axis relative to each of said signals, to identify an ST segment in each of said signals, to measure an ST deviation from said reference axis of each said ST segment, and to compare said ST deviation to a predetermined threshold ST deviation, said monitoring unit further having a memory to selectively store an anomalous ST deviation when said anomalous ST deviation exceeds said predetermined threshold ST deviation.

11. An apparatus for monitoring heart muscle electrical activity of a patient as recited in claim 10 further comprising:
    a data transmission unit in selective communication with said monitoring unit, said data transmission unit having a memory to receive said stored anomalous ST deviation from said memory of said monitoring unit and having a modem to transmit said stored anomalous ST deviation;
    a telephone line; and
    a remote central processing unit in selective communication with said modem across said telephone line for receiving said stored anomalous ST deviation and having printing means for displaying said stored anomalous ST deviation.

12. An apparatus for monitoring heart muscle electrical activity of a patient as recited in claim 10 wherein said monitoring unit is attached to a housing such that said housing and said monitoring unit are self-contained, portable and affixable to the patient.

13. A method for monitoring heart muscle electrical activity of a patient employing a portable monitoring unit affixable to the patient, the method comprising:
    obtaining electrical heart muscle signals generated by the patient and transmitting said signals to said monitoring unit;
    establishing a reference axis relative to each of said signals by means of said monitoring unit;
    identifying an ST segment in each of said signals by means of said monitoring unit;
    measuring an ST deviation from said reference axis for each said ST segment and comparing said ST deviation to a predetermined threshold ST deviation by means of said monitoring unit; and
    selectively storing an anomalous ST deviation when said anomalous ST deviation exceeds said predetermined threshold ST deviation by means of a memory within said monitoring unit.

14. A method for monitoring heart muscle electrical activity of a patient employing a portable monitoring unit affixable to the patient, the method comprising:
    obtaining electrical heart muscle signals generated by the patient and transmitting said signals to said monitoring unit;
    establishing a reference axis relative to each of said signals by means of said monitoring unit;
    identifying an ST segment in each of said signals by means of monitoring unit;
    measuring an ST deviation from said reference axis for each said ST segment;
    determining an average ST deviation from a plurality of ST deviations in sequence and comparing said average ST deviation to said predetermined threshold ST deviation within said monitoring unit; and
    storing a plurality of anomalous ST deviations in sequence having an average ST deviation exceeding said predetermined threshold deviation in a memory of said monitoring unit to the exclusion of ST deviations having an average ST deviation below said predetermined threshold ST deviation.

15. A method for monitoring heart muscle electrical activity of a patient as recited in claim 14 further comprising storing a first signal and a last signal of a sequence of heart muscle electrical signals embodying said plurality of anomalous ST deviations in sequence in said memory of said monitoring unit to the exclusion of signals embodying ST deviations having an average ST deviation below said predetermined threshold ST deviation.

16. A method for monitoring heart muscle electrical activity of a patient as recited in claim 15 further comprising downloading said memory of said monitoring unit into a memory of a data transmission unit, transmitting said first and last signals from said memory of said data transmission unit to a remote display unit, and creating a graphical display of said first and last signals versus time.

17. A method for monitoring heart muscle electrical activity of a patient as recited in claim 16 further comprising labeling with respect to each of said first and last signals a first time point on said graphical display where said reference axis is established and a second time point on said graphical display where said ST segment deviation is measured.

18. A method for monitoring heart muscle electrical activity of a patient as recited in claim 14 further comprising measuring a heart rate time history of said patient while measuring said plurality of anomalous ST deviations in sequence and storing said heart rate time history in said memory of said monitoring unit.

19. A method for monitoring heart muscle electrical activity of a patient as recited in claim 18 further comprising graphically correlating said heart rate time history of said patient and said plurality of anomalous ST deviations in sequence.

20. A method for monitoring heart muscle electrical activity of a patient as recited in claim 14 further comprising downloading said memory of said monitoring unit into a memory of a data transmission unit, transmitting said plurality of anomalous ST deviations in sequence from said memory of said data transmission unit to a remote display unit, and creating a graphical display of said plurality of anomalous ST deviations versus time.

* * * * *